(12) United States Patent
Yang

(10) Patent No.: US 12,605,505 B2
(45) Date of Patent: Apr. 21, 2026

(54) MINIATURE CLOSED-LOOP ARTIFICIAL PANCREAS SYSTEM

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 845 days.

(21) Appl. No.: 17/620,084

(22) PCT Filed: Dec. 31, 2019

(86) PCT No.: PCT/CN2019/130440
§ 371 (c)(1),
(2) Date: Dec. 16, 2021

(87) PCT Pub. No.: WO2021/012623
PCT Pub. Date: Jan. 28, 2021

(65) Prior Publication Data
US 2022/0305201 A1 Sep. 29, 2022

(30) Foreign Application Priority Data
Jul. 19, 2019 (WO) ................ PCT/CN2019/096673

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14532* (2013.01); *A61B 5/1473* (2013.01);
(Continued)

(58) Field of Classification Search
CPC ........ A61M 2230/201; A61M 2205/50; A61M 2005/14506; A61M 2005/14208;
(Continued)

(56) References Cited

U.S. PATENT DOCUMENTS

| | | | |
|---|---|---|---|
| 2003/0236498 A1 | 12/2003 | Gross et al. | |
| 2004/0153032 A1 | 8/2004 | Garribotto et al. | |

(Continued)

FOREIGN PATENT DOCUMENTS

| | | |
|---|---|---|
| CN | 1681544 | 10/2005 |
| CN | 104168935 | 11/2014 |

(Continued)

OTHER PUBLICATIONS

English translation of CN-106139311-A (Year: 2016).*

(Continued)

*Primary Examiner* — Bhisma Mehta
*Assistant Examiner* — Adam J. Cermak
(74) *Attorney, Agent, or Firm* — JCIP GLOBAL INC.

(57) ABSTRACT

The invention discloses a miniature closed-loop artificial pancreas system, comprising: infusion unit configured to deliver drugs; program unit comprising input end and output end, and the input end comprises a plurality of electrically connective regions for receiving signals of analyte data in the body fluid, after the output end is electrically connected to the infusion unit, according to the received signals of analyte data in the body fluid, the program unit controls whether the infusion unit delivers drugs; an infusion cannula with conductive area, the infusion cannula is the drug infusion channel; and a plurality of electrodes for detecting analyte data in body fluid, the electrode comprising conductive-area electrode and cannula-wall electrode, and one or more cannula-wall electrodes being located on/in the wall of (Continued)

the infusion cannula. It takes only one insertion to perform both analyte detection and drug infusion.

24 Claims, 13 Drawing Sheets

(51) Int. Cl.

| | |
|---|---|
| *A61B 5/145* | (2006.01) |
| *A61B 5/1473* | (2006.01) |
| *A61F 2/02* | (2006.01) |
| *A61M 5/14* | (2006.01) |
| *A61M 5/142* | (2006.01) |
| *A61M 5/145* | (2006.01) |
| *A61M 5/158* | (2006.01) |
| *A61M 5/20* | (2006.01) |
| *G16H 20/17* | (2018.01) |
| *G16H 40/63* | (2018.01) |

(52) U.S. Cl.
CPC ............ *A61B 5/4839* (2013.01); *A61F 2/022* (2013.01); *A61M 5/14236* (2013.01); *A61M 5/14244* (2013.01); *A61M 5/14248* (2013.01); *A61M 5/1452* (2013.01); *A61M 5/1454* (2013.01); *A61M 5/158* (2013.01); *A61M 5/172* (2013.01); *G16H 20/17* (2018.01); *G16H 40/63* (2018.01); *A61B 2560/0209* (2013.01); *A61B 2562/043* (2013.01); *A61M 5/1413* (2013.01); *A61M 2005/14208* (2013.01); *A61M 2005/14252* (2013.01); *A61M 2005/14268* (2013.01); *A61M 2005/14506* (2013.01); *A61M 2005/1585* (2013.01); *A61M 2005/1726* (2013.01); *A61M 2005/2006* (2013.01); *A61M 2205/0216* (2013.01); *A61M 2205/0233* (2013.01); *A61M 2205/0266* (2013.01); *A61M 2205/33* (2013.01); *A61M 2205/3317* (2013.01); *A61M 2205/3327* (2013.01); *A61M 2205/3553* (2013.01); *A61M 2205/3576* (2013.01); *A61M 2205/3592* (2013.01); *A61M 2205/50* (2013.01); *A61M 2205/502* (2013.01); *A61M 2209/088* (2013.01); *A61M 2230/005* (2013.01); *A61M 2230/20* (2013.01); *A61M 2230/201* (2013.01)

(58) Field of Classification Search
CPC ............ A61M 5/1413; A61M 5/14236; A61M 5/1723; A61B 5/14532; A61B 2562/04
See application file for complete search history.

(56) References Cited

U.S. PATENT DOCUMENTS

| | | | |
|---|---|---|---|
| 2005/0059871 A1 | 3/2005 | Gough et al. | |
| 2006/0253086 A1* | 11/2006 | Moberg | A61M 5/158 |
| | | | 604/272 |
| 2010/0256593 A1 | 10/2010 | Yodat et al. | |
| 2012/0277667 A1 | 11/2012 | Yodat et al. | |
| 2015/0112305 A1 | 4/2015 | Katase | |
| 2016/0136357 A1* | 5/2016 | Yang | A61M 5/14276 |
| | | | 604/66 |
| 2018/0126068 A1 | 5/2018 | Nazzaro et al. | |
| 2019/0117881 A1 | 4/2019 | Yang | |

FOREIGN PATENT DOCUMENTS

| | | |
|---|---|---|
| CN | 106139311 | 11/2016 |
| WO | 2008078319 | 7/2008 |
| WO | 2011064780 | 6/2011 |
| WO | 2017181324 | 10/2017 |

OTHER PUBLICATIONS

"International Search Report (Form PCT/ISA/210) of PCT/CN2019/130440," mailed on Apr. 24, 2020, pp. 1-4.
"Search Report of Europe Counterpart Application", issued on Jun. 23, 2023, p. 1-p. 8.

* cited by examiner

MINIATURE CLOSED-LOOP ARTIFICIAL PANCREAS SYSTEM

CROSS-REFERENCE TO RELATED APPLICATION

This application is a 371 of international application of PCT application serial no. PCT/CN2019/130440, filed on Dec. 31, 2019, which claims the priority benefits of PCT application serial no. PCT/CN2019/096673, filed on Jul. 19, 2019. The entirety of each of the above-mentioned patent applications is hereby incorporated by reference herein and made a part of this specification.

TECHNICAL FIELD

The present invention mainly relates to the field of medical instruments, in particular to a miniature closed-loop artificial pancreas system.

BACKGROUND

Diabetes is mainly a metabolic disease caused by abnormal human pancreatic function. Diabetes is a lifelong disease. At present, medical technology cannot cure diabetes. It can only control the occurrence and development of diabetes and its complications by stabilizing blood glucose. The normal human pancreas automatically monitors changes in the body's blood glucose levels and automatically secretes the required insulin. At present, the medical device for stabilizing blood glucose works by dynamically monitoring the blood glucose changes of the human body by a glucose sensor implanted in the subcutaneous tissue of the human body; and continuously accurately infusing insulin into the subcutaneous tissue of the human body through a medical cannula implanted in the subcutaneous tissue of the human body.

This method requires separately inserting glucose sensor and infusion cannula under the human skin. Even though there are some devices that can integrate the sensor probe and the infusion cannula into one device, the sensor and cannula still need to be separately inserted at different positions, increasing the risk of infection.

Therefore, there is a need in the prior art for a miniature closed-loop artificial pancreas system that can perform both detection and infusion at the same time.

BRIEF SUMMARY OF THE INVENTION

Embodiments of the present invention disclose a miniature closed-loop artificial pancreas system in which a plurality of electrodes are disposed on an infusion cannula comprising conductive area(s), and the infusion cannula itself acts as an electrode and infusion channel. It takes only one insertion to perform both analyte detection and drug infusion, thus reducing the risk of infection.

The invention discloses a miniature closed-loop artificial pancreas system, comprising: an infusion unit, the infusion unit includes drug storage unit(s), metal piece, piston(s) and rigid screw(s), the piston is arranged in the drug storage unit, metal piece, fixedly connected to a rigid screw, is arranged on the piston; rotating shaft, rotatable driving unit(s) and driving wheel(s) provided with wheel teeth, the driving unit includes one driving portion, and the driving unit can rotate around the rotating shaft, driving the driving portion to push the wheel teeth to rotate the driving wheel which engages the rigid screw to move forward in a non-rotating way; and power unit(s) and rebound unit(s), the power unit and the rebound unit apply force to the driving unit respectively to make the driving unit rotate reciprocally; position detector(s), the metal piece and the position detector interact to generate electrical or magnetic signals; program unit, the program unit comprising input end and output end, and the input end comprises a plurality of electrically connective regions for receiving signals of analyte data in the body fluid, after the output end is electrically connected to the infusion unit, according to the received signals of analyte data in the body fluid, the program unit controls whether the infusion unit delivers drugs, and convert received electrical or magnetic signals into piston position information; an infusion cannula with conductive area(s), the infusion cannula is the drug infusion channel; and a plurality of electrodes for detecting analyte data in body fluid, the electrode comprising conductive-area electrode(s) and cannula-wall electrode(s), the conductive area of the infusion cannula being at least as a conductive-area electrode, and one or more cannula-wall electrodes being located on/in the wall of the infusion cannula, when the infusion cannula is installed to the working position, the infusion cannula is connected with the infusion unit, the drug can then be injected into the body through the infusion cannula, and the different electrodes are electrically connected to different electrically connective regions respectively, inputting signal of analyte data in the body fluid to the program unit.

According to one aspect of this invention, cannula-wall electrode is located on the outer surface of the infusion cannula wall or in the infusion cannula wall.

According to one aspect of this invention, cannula-wall electrode is located on the outer surface of the infusion cannula wall, and when the infusion cannula is installed to the working position, the conductive-area electrode and the cannula-wall electrode are directly electrically connected to different electrically connective regions, respectively.

According to one aspect of this invention, cannula-wall electrode is located on the subcutaneous part of the outer surface of the infusion cannula wall, and the outer surface of the infusion cannula wall is further provided with electrode lead electrically connected to the cannula-wall electrode, and when the infusion cannula is installed to the working position, the electrode lead and the conductive-area electrode are electrically connected to different electrically connective regions, respectively.

According to one aspect of this invention, the infusion cannula includes an infusion steel needle and a hose which is placed on the outer wall surface of the infusion steel needle, and the needle cavity of the infusion steel needle is used for infusion of drugs.

According to one aspect of this invention, when the infusion cannula is installed to the working position, the depth of the hose into the skin is $d_1$, while the depth of the infusion steel needle into the skin is $d_2$, $d_1 \leq d_2$.

According to one aspect of this invention, the infusion steel needle is conductive-area electrode, and the cannula-wall electrode is located on the outer/inner surface of the hose wall, or is located on the outer wall surface of the infusion steel needle.

According to one aspect of this invention, when the infusion cannula is installed to the working position, the cannula-wall electrode located on the outer wall surface of the infusion steel needle is exposed in the subcutaneous tissue fluid or covered in whole or in part by the hose.

According to one aspect of this invention, when the cannula-wall electrode located on the outer wall surface of the infusion steel needle is covered in whole or in part by the hose, or when the cannula-wall electrode is located on the inner surface of the hose wall, the material of hose wall is permeable membrane or a semi-permeable membrane.

According to one aspect of this invention, the infusion cannula comprises a plurality of electrically conductive areas isolated from each other, the infusion cannula comprising a plurality of electrically conductive-area electrodes, different conductive-area electrodes being different conductive areas of the infusion cannula.

According to one aspect of this invention, the electrodes include working electrode and auxiliary electrode, and the number of the working electrode(s) and the auxiliary electrode(s) is one or more, respectively.

According to one aspect of this invention, conductive-area electrode is working electrode or auxiliary electrode.

According to one aspect of this invention, the auxiliary electrode is counter electrode, or the auxiliary electrode includes counter electrode and reference electrode.

According to one aspect of this invention, a plurality of electrodes form one or more electrode combinations, each electrode combination comprising working electrode and auxiliary electrode, the program unit choosing one or more electrode combinations to detect analyte data in body fluid.

According to one aspect of this invention, also comprises a remote device, the remote device and the program unit transmitting wireless signals to each other, the program unit transmitting the data of analyte in body fluid or the drug infusion information to the remote device, and the remote device sending the manually selected electrode combinations for detection or drug infusion instruction to the program unit.

According to one aspect of this invention, the input end is an elastic member, and the elastic member comprises one of or a combination of conductive strip, oriented conductive silica gel, conductive ring and conductive ball.

According to one aspect of this invention, the infusion unit includes a plurality of infusion subunits, the plurality of infusion subunits being electrically connected to the output ends, respectively, and the program unit controlling whether each infusion subunit delivers drugs.

According to one aspect of this invention, the miniature closed-loop artificial pancreas system is composed of a plurality of parts, the infusion unit and the program unit are arranged in different parts, and the different parts are connected by waterproof plugs.

According to one aspect of the present invention, the rigid screw is a metal screw, and the metal piece is electrically connected with the metal screw, so that the metal piece and the corresponding position detector constitute a capacitor, and the linear movement of the metal piece causes a change in capacitance making the corresponding position detector generate an electrical signal.

According to one aspect of the present invention, the metal piece is a magnetic metal piece, and the position detector is magnetic induction detector, the linear movement of the magnetic metal piece causes a change in the magnetic field around each position detector making each position detector generate a magnetic signal.

According to one aspect of the present invention, the direction in which the power unit applies a force to the driving unit is parallel to the forward direction of the rigid screw.

According to one aspect of the present invention, the infusion unit further includes two driving units and one driving wheel, the two driving units are coaxial, or the two driving units are respectively disposed on the two sides of the driving wheel.

According to one aspect of the present invention, the infusion unit further includes a clutch structure movably disposed on the driving wheel, the rigid screw passes through the clutch structure, and the clutch structure is provided with an internal thread that cooperates with the rigid screw, the driving wheel drives the clutch structure to rotate which, with the internal thread, engages the rigid screw to move forward in a non-rotating way.

According to one aspect of the present invention, the infusion unit further includes blocking wall(s), and the driving unit stops rotating upon contacting the blocking wall.

Compared with the prior arts, the technical solution of the present invention has the following advantages:

In the miniature closed-loop artificial pancreas system disclosed herein, firstly, the driving unit includes one driving portion, and the driving unit rotates to drive the driving portion to push the wheel teeth to rotate the driving wheel. Disposing one driving portion on the driving unit reduces the overall width of the driving unit and the driving unit's rotation amplitude, so that the internal structure of the infusion unit will be more compact, leading to reduced volume of the miniature closed-loop artificial pancreas system and lower production cost. Secondly, the infusion cannula includes conductive area. The conductive area is directly used as the detecting electrode, so that the infusion cannula performs analyte detection and drug infusion at the same time. Once the puncture is performed at one position, the analyte detection and the drug infusion can be completed simultaneously, reducing the risk of the user's infection. Thirdly, the miniature closed-loop artificial pancreas system is provided with a plurality of electrodes for detecting data of the body fluid analyte. The conductive area of the infusion cannula makes up at least one conductive-area electrode, and one or more cannula-wall electrodes are located in/on the wall of the infusion cannula. The conductive area of the infusion cannula acts as an electrode, so that the infusion cannula itself is an electrode, which reduces the difficulty of the electrode design process. At the same time, the plurality of electrodes located in/on the infusion cannula can also form specific electrode combinations while completing the detection of the analyte data, so that the program unit or the user can select one or part of them according to actual needs. In addition, when the infusion cannula is installed to the working position, the infusion cannula connects with the infusion unit to allow the drugs to flow through the infusion cannula into the body, and the different electrodes are electrically connected to different electrically connective regions inputting the analyte data signal to the program unit. With this design method, after the user attaches the miniature closed-loop artificial pancreas system to the skin surface, the mounting unit for installing the infusion cannula is pressed. When the infusion cannula is installed to the working position, the miniature closed-loop artificial pancreas system can begin to work. This approach reduces the users pre-using steps and improves the user experience.

Furthermore, the infusion cannula comprises an infusion steel needle and a hose placed on the outer wall surface of the infusion steel needle, and the needle cavity of the infusion steel needle is used for drug infusion. The process of designing the electrodes on the surface of the hose is relatively simple, so that this design reduces the difficulty of the electrode manufacturing process and improves the preparation efficiency. Secondly, the wall material of the hose can be selected according to needs, and the wall of the cannula can only allow specific analytes to pass through, weaken the interference of other substances, and improve the accuracy of analyte data detection.

Furthermore, when the cannula-wall electrode located on the outer wall surface of the infusion steel needle is covered in whole or in part by the hose, or when the cannula-wall electrode is located on the inner surface of the hose wall, the hose wall is a permeable membrane or a semi-permeable membrane. The hose wall material is selected from a permeable membrane or a semi-permeable membrane to ensure the required analyte passes through the hose wall to the electrode surface. It can improve the flexibility of electrode position design without affecting the detection.

Furthermore, the infusion cannula comprises a plurality of electrically insulated conductive areas, the infusion cannula comprises a plurality of conductive-area electrodes, and the different conductive-area electrodes are different conductive areas of the infusion cannula. The different conductive areas of the infusion cannula itself serve as electrodes, which can further reduce the number of electrodes on the surface of the cannula wall and simplify the manufacturing process of the infusion cannula.

Furthermore, a plurality of electrodes constitute one or more electrode combinations, each electrode combination includes working electrode and auxiliary electrode, and the program unit selects one or more electrode combinations to detect the body fluid analyte data. On the one hand, when a combination of electrodes fails to detect, the program unit can select other electrode combinations for detection according to the situation to ensure the detection process of the body fluid signal is uninterrupted. On the other hand, the program unit can select multiple electrode combinations to work at the same time, performing statistical analysis on multiple sets of data of the same parameter at the same time, improving the detection accuracy of the analyte data, and then issue a more accurate infusion signal.

Furthermore, the infusion unit comprises a plurality of infusion subunits, the plurality of infusion subunits being electrically connected to the output end respectively, and the program unit controlling whether each infusion subunit delivers drugs. Different drugs are reserved in different infusion subunits, and the program unit sends different drug infusion instructions to different infusion subunits to achieve precise control of the analyte level in body fluid.

Furthermore, the direction in which the power unit applies a force to the driving unit is parallel to the forward direction of the rigid screw. Such a design can make full use of the internal structural layout of the infusion unit, reduce the space required for mechanical operation of the power unit, and thereby reduce the volume of the miniature closed-loop artificial pancreas system.

Furthermore, the infusion unit includes two driving units and one driving wheel, the two driving units are coaxial, or the two driving units are respectively disposed on the two sides of the driving wheel. The two driving units and one driving wheel cooperate with each other, which reduces the rotation amplitude of the driving unit, making the internal structure of the infusion unit more compact, and further reducing the volume of the miniature closed-loop artificial pancreas system. At the same time, the two driving units cooperating with each other can improve the infusion accuracy of the device, so that the amount of infused drugs can be controlled precisely.

DETAILED DESCRIPTION

Figure 1:
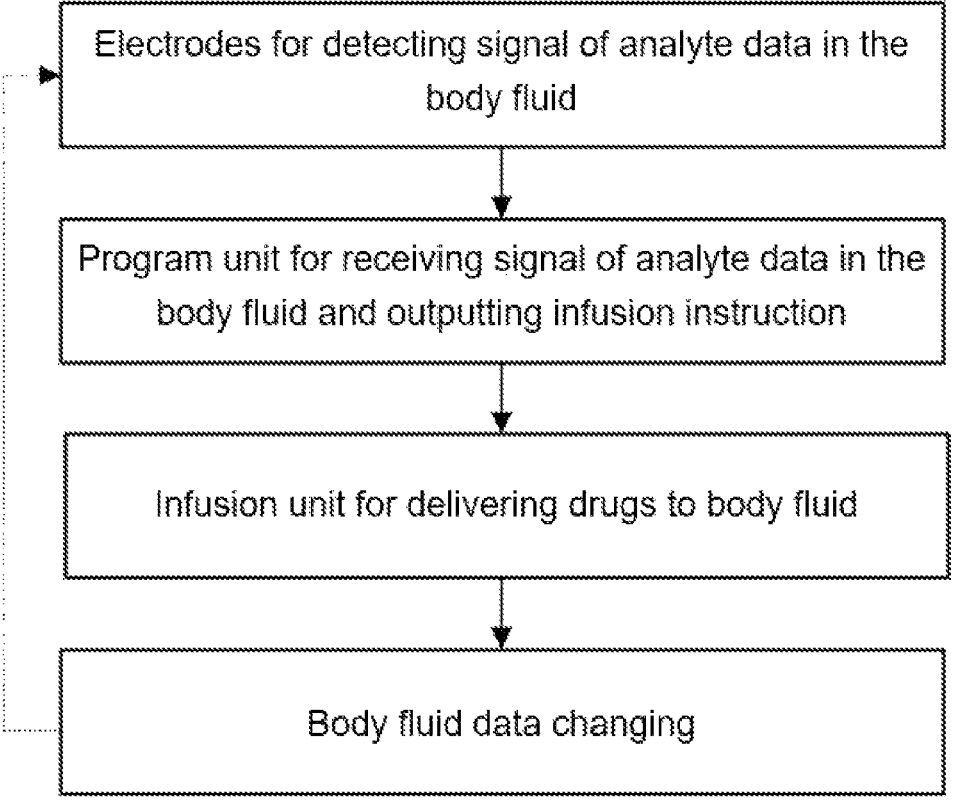
FIG. 1 is a flow chart of the operation of a miniature closed-loop artificial pancreas system according to an embodiment of the present invention.

As described above, in the prior art device, the detection and the infusion are performed separately to control the analyte level in the body fluid, and it is necessary to puncture at multiple positions on the skin, thereby increasing the pain of the user and increasing the risk of infection.

The study found that the cause of the above problems is that the sensor detection device and the drug infusion device are two independent units. Or even if the two are designed into a single structure, a plurality of puncture positions are still required on the body surface.

In order to solve this problem, the present invention provides a miniature closed-loop artificial pancreas system, the infusion cannula contains conductive area, which makes the infusion cannula itself as an electrode for detecting analyte data and a drug infusion channel. And it can perform detection and infusion with only one puncture.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in the following description of the drawings.

FIG. 1 is a flow chart showing the operation of a miniature closed-loop artificial pancreas system according to an embodiment of the present invention.

The miniature closed-loop artificial pancreas system of the embodiment of the invention comprises three basic parts: electrodes, a program unit and an infusion unit. The body fluid analyte data is obtained by the electrodes and converted into an electrical signal. Electrical signals are passed to the program unit via electrodes and/or electrode leads. After analyzing the body fluid analyte data signal, the program unit sends a signal to the infusion unit controlling whether to perform a drug infusion, thereby stabilizing the body fluid parameters. The body fluid analyte data are detected by the electrodes in real time, and the cycle of detection and infusion is without interruption. This process does not require human intervention and is done directly through program analysis to control the stability of body fluid parameters.

Figure 2A:
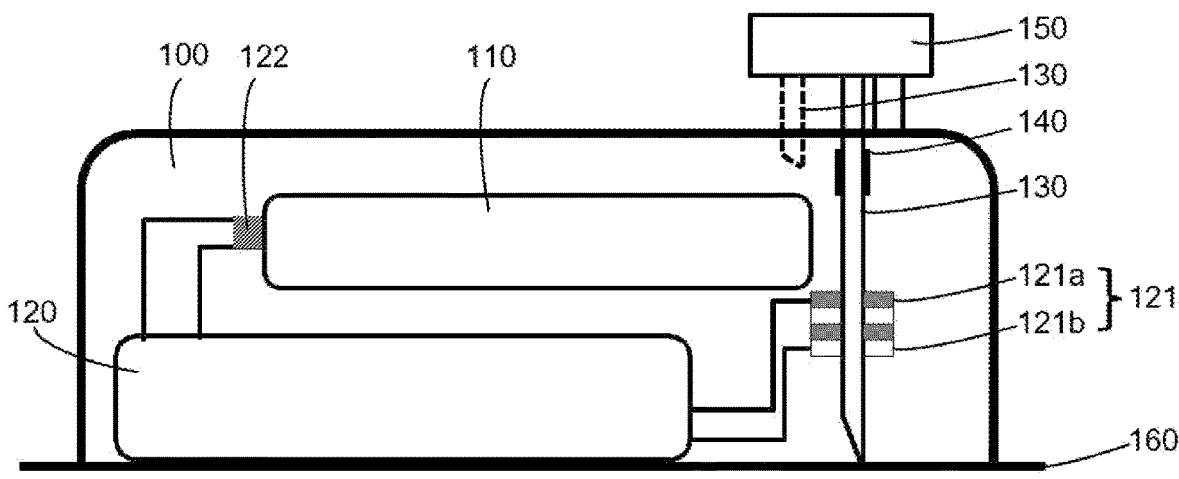
FIG. 2a is a schematic cross-sectional view of an infusion cannula of a miniature closed-loop artificial pancreas system in a pre-installation position according to one embodiment of the present invention.
Figure 2B:
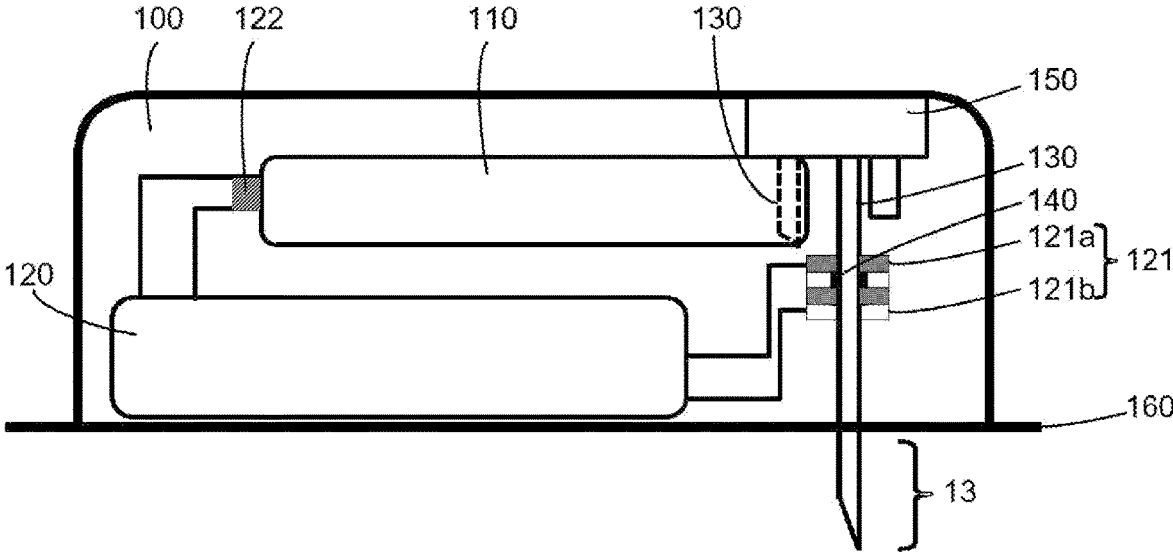
FIG. 2b is a schematic cross-sectional view showing the infusion cannula of the miniature closed-loop artificial pancreas system in a working position according to an embodiment of the present invention.

FIG. 2a-FIG. 2b are cross-sectional views of a miniature closed-loop artificial pancreas system 100 according to an embodiment of the present invention, and the miniature closed-loop artificial pancreas system 100 is an integral structure. FIG. 2a shows the infusion cannula 130 in the pre-installation position while FIG. 2b shows the infusion cannula 130 in the working position.

Program unit 120 includes an input end 121 and an output end 122. The input end 121 is used for receiving a body fluid analyte data signal. In the embodiment of the invention, the input end 121 includes electrically connective regions 121a and 121b. When in operation, the electrically connective region is electrically connected to the electrode or electrode lead to receive the analyte signal. In other embodiments of the invention, the input end 121 may also include more electrically connective regions depending on the number of electrodes. The output end 122 is electrically coupled to the infusion unit 110, allowing the program unit 120 to effectively control the infusion unit 110.

During the use of the miniature closed-loop artificial pancreas system of the embodiment of the present invention, the infusion cannula 130 can slide relative to the input end 121, while the input end 121 is provided as an elastic member. The elastic member is to ensure an interference fit between the infusion cannula 130 and the input end 121 to avoid poor electrical contact. The elastic member includes: conductive rubber strip, oriented conductive silica gel, conductive ring, conductive ball, etc. When the number of electrodes is relatively large, the electrically connective regions are relatively dense. In this case, according to different structural designs, the elastic members may be one or more combinations of the above.

In an embodiment of the invention, the infusion cannula 130 is mounted on the mounting unit 150. When the infusion cannula 130 is in the pre-installation position, the mounting unit 150 protrudes from the outer surface of the miniature closed-loop artificial pancreas system 100, as shown in FIG. 2a. When the infusion cannula 130 is installed to the working position, the mounting unit 150 is pressed into the miniature closed-loop artificial pancreas system 100 with the top portion integral with the miniature closed-loop artificial pancreas system 100 housing, as shown in FIG. 2b. Prior to use by users, the mounting unit 150 holds the infusion cannula 130 in the pre-installation position. After the miniature closed-loop artificial pancreas system 100 is attached on the surface of the human body, the mounting unit 150 is pressed to insert the infusion cannula under skin, and the miniature closed-loop artificial pancreas system can start operation. Compared with other infusion cannula installation methods, the installation method of the embodiment of the invention reduces the steps required for installation, makes the installation more convenient and flexible and improves the user experience.

The manner of setting the infusion cannula 130 in the mounting unit 150 can be various, and is not specifically limited herein. Specifically, in the embodiment of the present invention, the other side of the mounting unit 150 also protrudes from the portion of infusion cannula 130 (shown by a dotted line in FIG. 2a and FIG. 2b) for subsequent connection with the outlet of the infusion unit 110 to achieve drug circulation.

In an embodiment of the invention, the infusion cannula 130 includes one or more electrically conductive areas. Here, the conductive area refers to different areas in/on the wall of infusion cannula 130, and the cannula wall itself is electrically conductive. The material of the conductive area includes stainless steel, metal alloy or other conductive materials, and is not specifically limited herein. Specifically, in the embodiment of the present invention, the whole material of the infusion cannula 130 is stainless steel. At this time, the infusion cannula 130 as a whole has one conductive area. The infusion cannula 130 itself acts as an electrode and can reduce the number of electrodes and simplify the electrode design process.

In other embodiments of the invention, the infusion cannula 130 further includes an electrical contact region 140 coupled to the input end 121. As shown in FIG. 2a, the electrical contact region 140 is not electrically coupled to the input end 121 when the infusion cannula 130 is in the pre-installation position. And the other end of the infusion cannula 130 is also not connected with the infusion unit 110 outlet. As shown in FIG. 2*b*, when the infusion cannula 130 is mounted to the working position, one end of the infusion cannula 130 is inserted subcutaneously (indicated by the solid line portion of the infusion cannula in FIG. 2*b*) and the other end (illustrated by the dotted portion of the infusion cannula in FIG. 2*b*) is connected with the outlet of the infusion unit 110, thereby establishing a flow path for the drug from the infusion unit 110 to the body tissue fluid. At the same time, the electrical contact region 140 reaches the electrically connective region of the input end 121, enabling electrical connection between the program unit 120 and the electrical contact region 140.

It should be noted that even if the infusion cannula 130 and the infusion unit 110 are connected, and the input end 121 and the electrical contact region 140 of the infusion cannula 130 are electrically connected, as long as the infusion cannula 130 does not penetrate the skin, the program unit 120 will not enter working mode, so that the miniature closed-loop artificial pancreas system does not generate any analyte data signal, nor does it issue an instruction to inject drug. Therefore, in other embodiments of the present invention, when the infusion cannula 130 is in the pre-installation position, the electrical contact region 140 may also be electrically connected to the electrically connective region of the input end 121 or the infusion cannula 130 may be coupled to the outlet of the infusion unit 110. And there are no specific restrictions herein.

In an embodiment of the invention, a medical tape 160 for attaching the miniature closed-loop artificial pancreas system 100 to the skin surface is used to paste the program unit 120, the infusion unit 110, the electrode and the infusion cannula 130 as a whole on the skin. When the infusion cannula 130 is installed to the working position, the portion of the infusion cannula 130 that is inserted into the skin is 13.

Figure 3A:
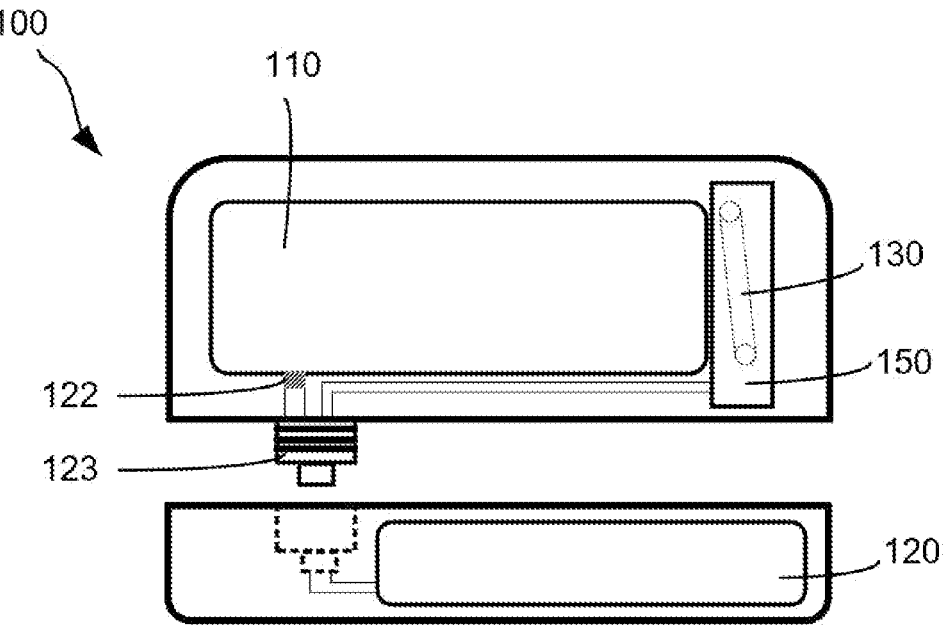
FIG. 3a-FIG. 3b are top views of a miniature closed-loop artificial pancreas system in accordance with another embodiment of the present invention.

FIG. 3*a* is a top view of a miniature closed-loop artificial pancreas system 100 in accordance with another embodiment of the present invention.

In one embodiment of the invention, the miniature closed-loop artificial pancreas system 100 comprises two parts. The program unit 120 is disposed in one part, the infusion unit 110 is disposed in another part, and the two parts are electrically connected by the waterproof electrical plug 123. The part of the infusion unit 110 can be discarded after being used once, and the part of the program unit 120 can be reused, saving the users cost.

In other embodiments of the present invention, the miniature closed-loop artificial pancreas system 100 may also be composed of more parts, and parts that do not require electrical connection may be connected using a common waterproof plug.

Figure 3B:
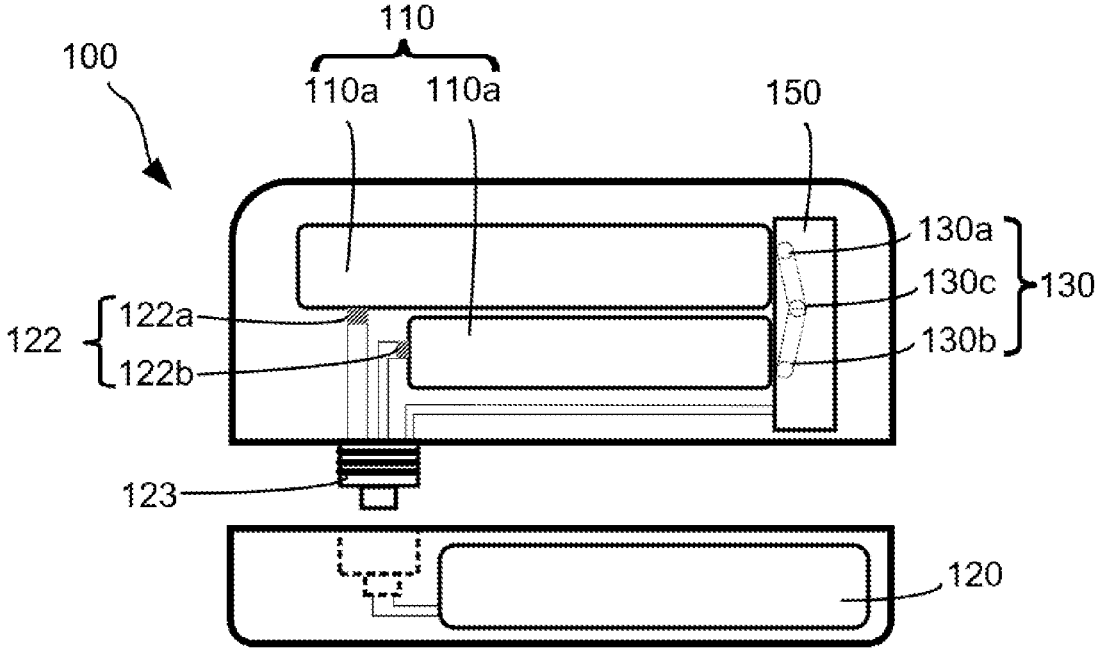

FIG. 3*b* is a top view of a miniature closed-loop artificial pancreas system 100 in accordance with another embodiment of the present invention.

In an embodiment of the invention, the miniature closed-loop artificial pancreas system 100 comprises two parts, and the infusion unit 110 comprises two infusion subunits 110*a* and 110*b*. The infusion subunits 110*a* and 110*b* can be used to reserve different drugs such as insulin, glucagon, antibiotics, nutrient solution, analgesics, morphine, anticoagulants, gene therapy drugs, cardiovascular drugs or chemotherapeutic drugs, etc. Infusion subunits 110*a* and 110*b* are electrically coupled to outputs 122*a* and 122*b*, respectively, allowing the program unit 120 to effectively control the infusion unit 110. The outlets of infusion subunits 110*a* and 110*b* can be connected with the 130*a* portion and 130*b* portion of infusion cannula respectively. 130*a* and 130*b* are connected with the 130*c* portion of infusion cannula, respectively. The 130*c* portion of the infusion cannula is used to penetrate the skin, thereby establishing a path for the two drugs to flow from the infusion unit 110 into the body fluid. That is, the miniature closed-loop artificial pancreas system still penetrates the skin only in one position. In the embodiment of the present invention, after the body fluid analyte data signal is transmitted to the program unit 120, program unit 120 can output different infusion signals to different infusion subunits to control whether infusion of drug is required. This method realizes accurate detection and control of body fluid analyte level to stabilize the physiological state of the user.

In other embodiments of the present invention, there may be more infusion subunits according to actual needs, and multiple infusion subunits may be disposed in different parts of the miniature closed-loop artificial pancreas system 100. There are no specific restrictions herein.

Figure 4:
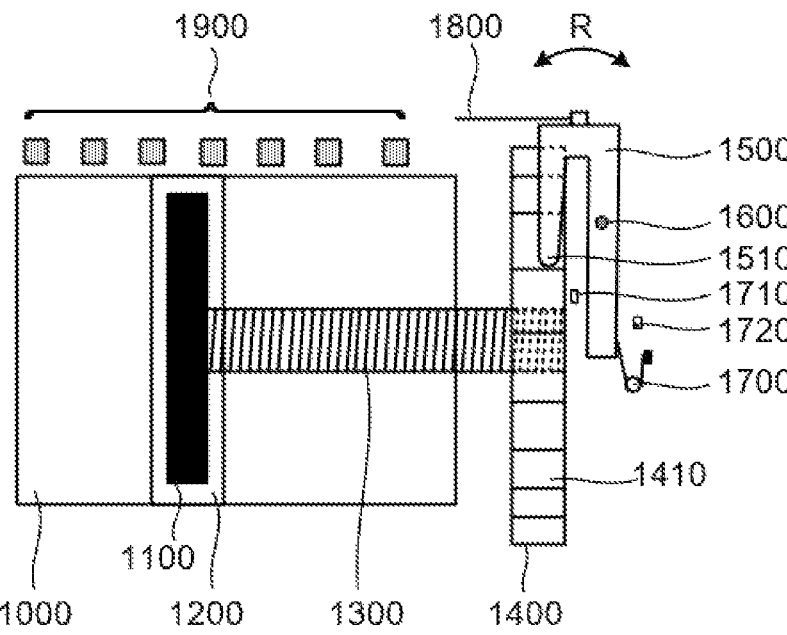
FIG. 4 is a schematic diagram of the main structure of an infusion unit according to one embodiment of the present invention.
Figure 5:
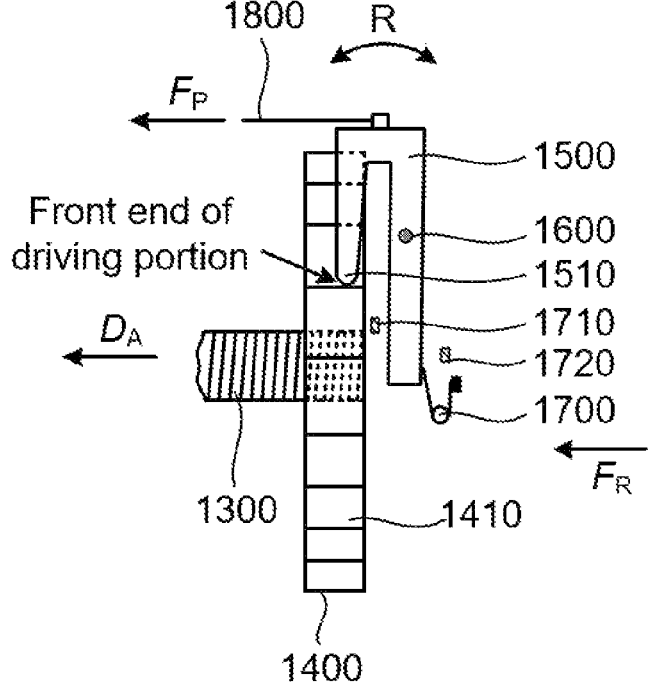
FIG. 5 is a schematic structural diagram of cooperation between a driving unit and a driving wheel according to another embodiment of the present invention.

Please refer to FIG. 4-FIG. 5. FIG. 4 is a schematic main structural diagram of an infusion unit of a miniature closed-loop artificial pancreas system. FIG. 5 is a schematic structural diagram of the driving portions 1510*a* and 1510*b* in FIG. 4, pushing the wheel teeth 1410.

The internal structure of the infusion unit mainly includes the drug storage unit 1000, the piston 1200, the rigid screw 1300, the driving wheel 1400, the driving unit 1500, the rotating shaft 1600, the rebound unit 1700 and the power unit 1800.

The piston 1200 is used to infuse liquid drug into the body.

The rigid screw 1300 is connected to the piston 1200 and the driving wheel 1400, respectively. In the embodiment of the present invention, the driving wheel 1400 advances the rigid screw 1300 forward by screwing, the rigid screw 1300 then forces the piston 1200, arranged in the drug storage unit 1000, to move forward, so as to achieve the purpose of drug infusion.

The peripheral surface of the driving wheel 1400 is provided with wheel teeth 1410. The wheel teeth 1410 are gear teeth or ratchet teeth. Specifically, in the embodiment of the present invention, for improving driving efficiency, the wheel teeth 1410 are ratchet teeth which can be pushed more easily.

One driving portion 1510 is provided at one end of the driving unit 1500 to push the wheel teeth 1410 and thereby rotate the driving wheel 1400. The driving unit 1500 is movably connected to the rotating shaft 1600, and is also connected with the power unit 1800 and the rebound unit 1700, respectively. The power unit 1800 and the rebound unit 1700 cooperate with each other to make the driving unit 1500 rotate reciprocally around the rotating shaft 1600, as shown in the R direction in FIG. 5. When the driving unit 1500 performs one reciprocal rotation, the driving wheel 1400 drives the rigid screw 1300 forward by one step, and the rigid screw 1300 engages the piston 1200 to infuse one unit of drug.

In the embodiment of the present invention, the rebound unit 1700 is a spring. In other embodiments of the present invention, the rebound unit 1700 can also be an elastic piece, an elastic plate, an elastic rod, etc. The type and material selection of the rebound unit 1700 are not specifically limited herein, as long as it can satisfy the condition of making the driving unit 1500 rotate in the return direction.

The power unit 1800 is a linear actuator. In the embodiment of the present invention, the power unit 1800 is an electrically driven linear actuator or an electrically heated linear actuator. By alternately turning on and off, the power unit 1800 outputs power in pulses. In other embodiments of the present invention, the power unit 1800 may be other types, eg. mini-airbag.

In the embodiment of the present invention, when the power unit 1800 pulls the driving unit 1500 by force $F_P$, the driving unit 1500 rotates counter-clockwise around the rotating shaft 1600, driving the driving portion 1510 to push the wheel teeth 1410 forward, and thereby making the driving wheel 1400 rotate. The driving wheel 1400 then moves the rigid screw 1300 forward in the $D_A$ direction. At this time, the rebound unit 1700 builds a gradually increasing elastic force $F_R$. When the power unit 1800 stops applying force and under the action of only the elastic force $F_R$, the driving unit 1500 will rotate clockwise around the rotating shaft 1600. At this time, the driving portion 1510 stops pushing the wheel tooth 1410, but just slides on the surface of the adjacent wheel tooth 1410 until it slides to the next driving position, and the driving wheel 1400 stop rotating. The driving unit 1500 completes one reciprocal rotation.

It should be noted here that in order to minimize the impact of manufacturing tolerances and ensure that the wheel teeth 1410 can be pushed during each reciprocal rotation for infusion safety, after the driving portion 1510 slides to the next driving position, the driving unit 1500 can be further rotated clockwise by an appropriate distance to move the driving portion 1510 slightly away from the driving position.

Preferably, in the embodiment of the present invention, the direction of $F_P$, the direction of $F_R$ and the direction of $D_A$ are parallel to one another. This parallel design can make full use of space and optimize the structural relationships inside the infusion unit, making the internal structure more compact. In other embodiments of the present invention, the $F_P$ direction and the $F_R$ direction may not be parallel, which is not specifically limited herein, as long as the purpose of making the driving unit 1500 reciprocate can be achieved.

In the embodiment of the present invention, blocking walls 1710 and 1720 that can stop the driving unit 1500 from rotating are also provided. And an electrical signal may be triggered when the driving unit 1500 contacts the blocking wall 1710 or 1720, allowing the program unit to control the power output of the power unit 1800. In another embodiment of the present invention, only the blocking wall 1710 or only the blocking wall 1720 may be provided, so that the driving unit 1500 can stop rotating in either direction. Blocking wall(s) in combination with a time controller allow the program unit to control the power output of the power unit 1800. In another embodiment of the present invention, no blocking wall is provided, and the rotation of the driving unit 1500 is completely controlled by a time controller in the program unit.

It should be noted that, the position of the blocking wall 1710 or 1720 is not specifically limited in the embodiment of the present invention, as long as the condition that the driving unit 1500 stops rotating can be satisfied.

Figure 6A:
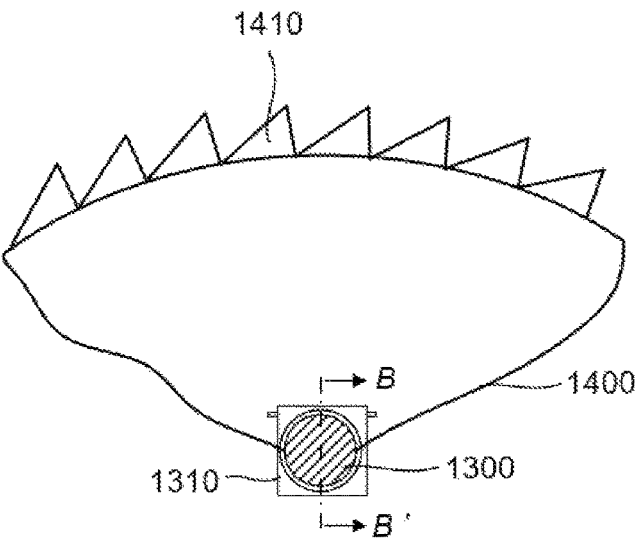
FIG. 6a-FIG. 6b are schematic diagrams of the clutch structure under different perspectives according to one embodiment of the present invention.
Figure 6B:
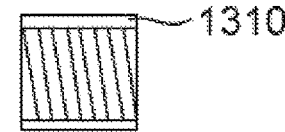

FIG. 6a-FIG. 6b are schematic structural diagrams of a clutch structure 1310 according to an embodiment of the present invention. FIG. 6b is a schematic cross-sectional view of the clutch structure 1310 taken along the line B-B' in FIG. 6a.

The embodiment of the present invention further includes a clutch structure 1310. The clutch structure 1310 is disposed at the central position of the driving wheel 1400, and the rigid screw 1300 passes through the clutch structure 1310. The clutch structure 1310 is provided with an internal thread matching the external thread of the rigid screw 1300, as shown in FIG. 6b. During drug infusion, the driving wheel 1400 drives the clutch structure to rotate synchronously, and the clutch structure advances the rigid screw 1300 forward through the internal thread. Obviously, in the embodiment of the present invention, the rigid screw 1300 only advances in its own axial direction without rotating. In another embodiment of the present invention, the driving wheel 1400 has an internal thread, which can directly cooperate with the external thread of the rigid screw 1300.

Figure 7:
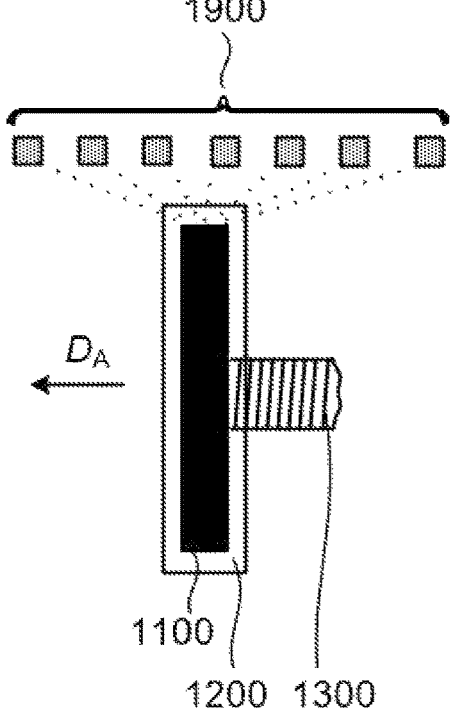
FIG. 7 is a schematic structural diagram of a piston and a position detector according to one embodiment of the present invention.

FIG. 7 is a schematic structural diagram of a metal piece 1100 and a position detector 1900 according to an embodiment of the present invention.

The infusion unit according to the embodiment of the present invention further includes one or more position detectors 1900. The position detector 1900 interacts with the metal piece 1100 to detect the position of the metal piece 1100, and thereby determine the position of the piston 1200 to calculate the remaining amount of drug in the drug storage unit 1000. Specifically, in the embodiment of the present invention, the metal piece 1100 is a magnetic metal piece, and the position detector 1900 is magnetic position detector. When the metal piece 1100 is located at a certain position, the location of every position detector 1900 has a certain magnetic field size and direction, allowing the position of the piston 1200 to be accurately detected. When the piston 1200 is moving, the magnitude and direction of the magnetic field at the location of every position detector 1900 changes accordingly, in which way the position of the piston 1200 is detected in real time. The position detector 1900 sends magnetic signal(s) or magnetic signal change to the program unit. After processed, the signal is converted into position information of the piston 1200, which is then used to calculate the remaining drug amount.

According to the specifications of the drug storage unit 1000, the number of the position detectors 1900 can be one, two or more. Specifically, in the embodiment of the present invention, the number of the position detectors 1900 is seven. In another embodiment of the present invention, the number of the position detectors 1900 is two. In still another embodiment of the present invention, only one position detector 1900 is provided.

It should be noted that when there are more than two position detectors 1900, preferably, the position detectors 1900 are linearly and equally spaced. The position detector 1900 can be disposed in the infusion unit, or at a position, corresponding to the changing position of the piston 1200, in the program unit, or embedded in the side wall of the drug storage unit 1000, or located on the inner surface of the drug storage unit 1000. The position detectors 1900 may also be arranged in other ways, which are not specifically limited herein, as long as the conditions for detecting the position of the piston 1200 can be satisfied.

As previously mentioned, the rigid screw 1300 only moves along its own axial direction without rotating. Therefore, the metal piece 1100, embedded in the piston 1200 and fixedly connected to the rigid screw 1300, can also be advanced non-rotating only along the axial direction of the rigid screw 1300. Compared with detecting position with a rotating screw, the embodiment of the present invention only detects magnetic field signal(s) in one-dimensional axial direction or two-dimensional plane (determined by the moving direction of the screw and a detector). The detecting principle, the operation and structural design are much simpler, and the position information is more accurate, reducing the cost of design and production.

Figure 8A:
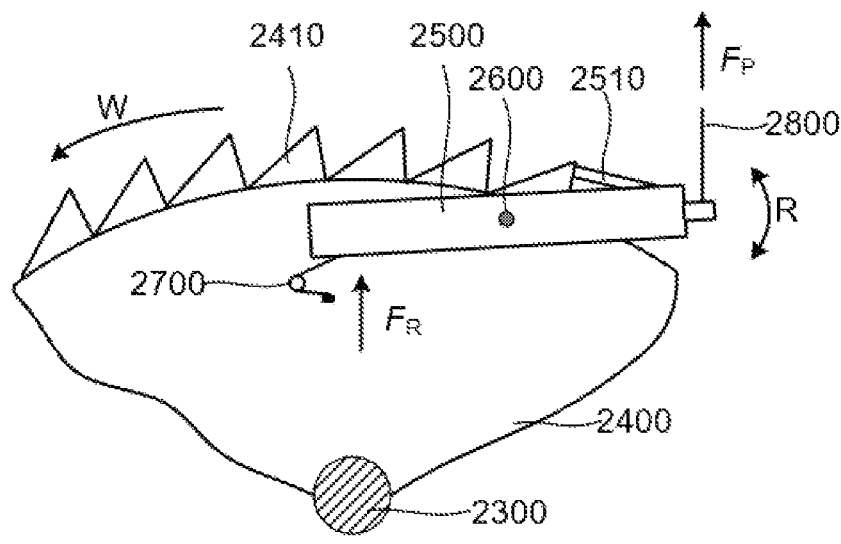
FIG. 8a-FIG. 8b are schematic structural diagrams of cooperation between a driving unit and a driving wheel according to another embodiment of the present invention.
Figure 8B:
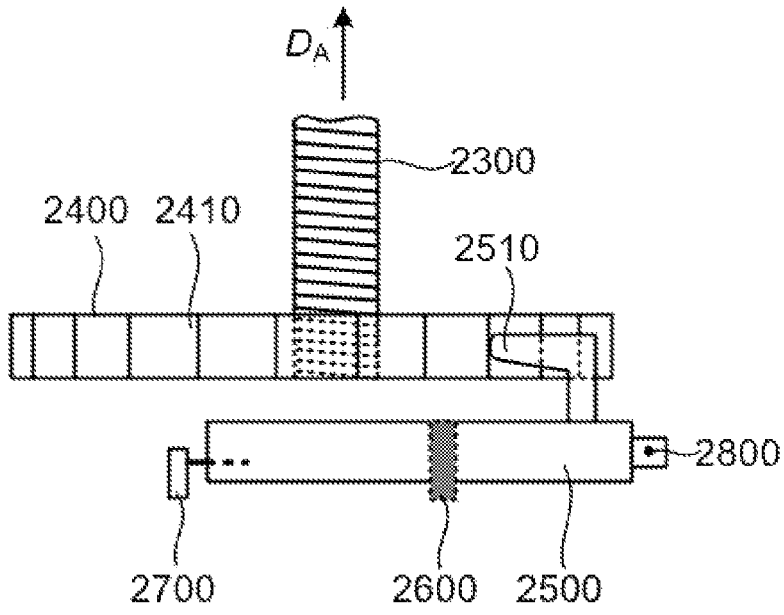

FIG. 8a-FIG. 8b are schematic structural diagrams of the driving portion 2510 pushing the wheel teeth 2410 to move according to another embodiment of the present invention. The difference between this embodiment and the foresaid embodiment is that the direction of the power unit pulling force $F_P$ is perpendicular to the forward direction $D_A$ of the rigid screw 2300, and other structural designs are the same as those in the foresaid embodiment.

FIG. 8a is a view along the axial direction of the rigid screw 2300, and FIG. 8b is a schematic plan view of the structure of FIG. 8a. The rotating shaft 2600 and the rebound unit 2700 are provided on the base (not shown). As described above, the driving unit 2500 rotating reciprocally in the R direction drives the driving portion 2510 to push the wheel teeth 2410, causing the driving wheel 2400 to rotate in the W direction, and to drive the rigid screw 2300 to advance in the $D_A$ direction. The driving principle of the driving unit 2500 according to the embodiment of the present invention is consistent with the foresaid embodiment, and details are not described herein again.

Figure 9:
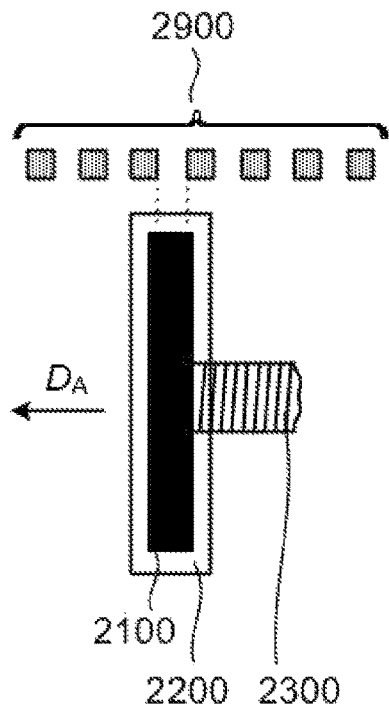
FIG. 9 is a schematic structural diagram of a piston and a position detector according to another embodiment of the present invention.

FIG. 9 is a schematic structural diagram of metal piece 2100 and position detector 2900 according to an embodiment of the present invention.

In the embodiment of the present invention, the rigid screw 2300 is made of metallic material. The metal piece 2100 is fixedly and electrically connected to the rigid screw 2300. At a certain position, the metal piece 2100 and a corresponding position detector 2900 will form a capacitor to generate electrical signal(s). When the piston 2200 moves, the capacitance changes with the area of the electrode plate, and the corresponding position detector 2900 generates a changed electrical signal to accurately detect the position of the piston 2200. The corresponding position detector 2900 transmits the electrical signal to the program unit to be converted to the position information of the piston 2200. And then the program unit outputs the remaining drug amount. Specifically, in the embodiment of the present invention, for accurate position detection, a plurality of position detectors 2900 are provided, and the setting manner thereof is as described above.

Figure 10:
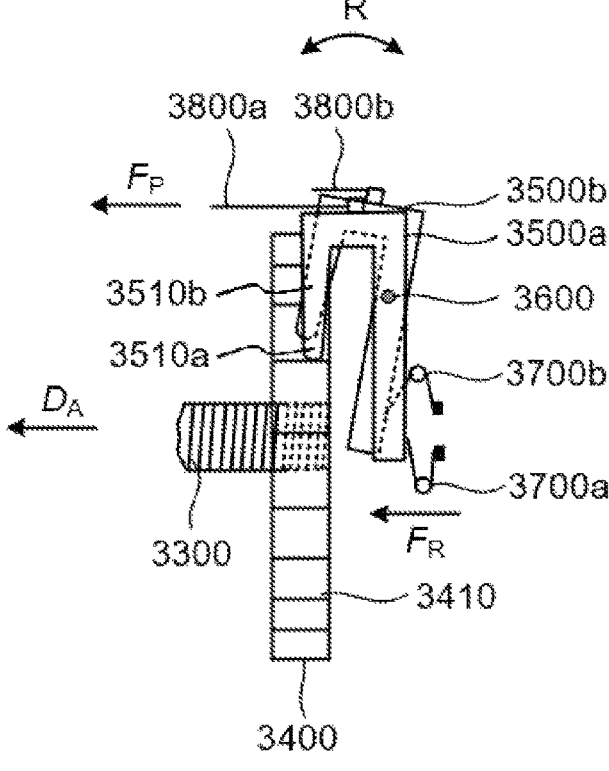
FIG. 10 is a schematic structural diagram of cooperation between a driving unit and a driving wheel according to another embodiment of the present invention.

FIG. 10 is a schematic structural diagram of the driving portion 3510a or 3510b pushing the wheel teeth 3410 to move according to another one embodiment of the present invention. The difference from the previous embodiment is that two driving units 3500a and 3500b are provided which can rotate coaxially The driving unit 3500a rotates reciprocally in the R direction around the rotating shaft 3600 under the action of the power unit 3800a and the rebound unit 3700a. Similarly, the driving unit 3500b rotates reciprocally in the R direction around the rotating shaft 3600 under the action of the power unit 3800b and the rebound unit 3700b. In the embodiment of the present invention, the rotations of the two driving units do not interfere with each other.

Preferably, in the embodiment of the present invention, the driving unit 3500a and the driving unit 3500b rotate asynchronously. That is, when the driving portion 3510a of the driving unit 3500a pushes the wheel teeth 3410 to move, the driving portion 3510b of the driving unit 3500b slides on the surface of the wheel teeth 3410. When the driving portion 3510b slides to the driving position of the next wheel tooth 3410, the program unit controls the power unit 3800a to stop outputting power to the driving unit 3500a, and in turn controls the power unit 3800b to output power to the driving unit 3500b. At this time, the driving unit 3500a rotates in the clockwise direction under the action of the rebound unit 3700a, and the driving portion 3510a slides on the surface of the wheel teeth, while the driving portion

3510b pushes the wheel teeth 3410. The driving units 3500a and 3500b are alternately powered to push the driving wheels 3400.

In the embodiment of the present invention, the pulling force $F_P$ of the power units 3800a and 3800b, the elastic force $F_R$ of the rebound units 3700a and 3700b and the forward direction $D_A$ of the rigid screw 3300 are shown in the figure. Like foresaid statement, the direction of the pulling force $F_P$ is parallel to the forward direction $D_A$ of the rigid screw 3300.

Figure 11:
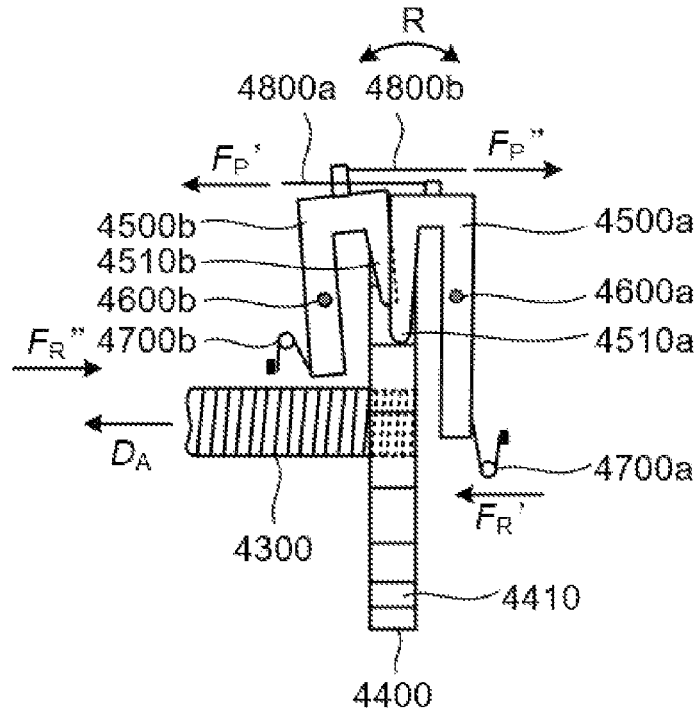
FIG. 11 is a schematic structural diagram of cooperation between a driving unit and a driving wheel according to another embodiment of the present invention.

FIG. 11 is a schematic structural diagram of a driving portion 4510a or 4510b pushing the wheel teeth 4410 according to another one embodiment of the present invention. This embodiment is different from the foresaid embodiment in that the driving units 4500a and 4500b are respectively disposed on both sides of the driving wheel 4400.

Similarly to the above, the driving portions 4510a and 4510b alternately push the wheel teeth 4410, respectively, and the power output of the power units 4800a and 4800b are both controlled by the program unit.

It should be noted that, in the embodiment of the present invention, the direction of the pulling force $F_P'$ of the power unit 4800a and the direction of the pulling force $F_P''$ of the power unit 4800b are opposite. Obviously, the direction of the returning force $F_R'$ of the rebound unit 4700a and the direction of the returning force $F_R''$ of the rebound unit 4700b are also opposite.

Also, in the embodiment of the present invention, the driving units 4500a and 4500b rotate asynchronously. That is, when the driving portion 4510a of the driving unit 4500a pushes the wheel teeth 4410 to move, the driving portion 4510b of the driving unit 4500b slides on the surface of the wheel teeth 4410. When the driving portion 4510b slides to the driving position of the next wheel tooth 4410, the program unit controls the power unit 4800a to stop outputting power to the driving unit 4500a, and in turn controls the power unit 4800b to output power to the driving unit 4500b. The driving unit 4500a returns to the clockwise rotation by the rebound unit 4700a, while the driving portion 4510a slides on the surface of the wheel teeth 4410, and the driving portion 4510b pushes the wheel teeth 4410. The driving units 4500a and 4500b alternately pushes the driving wheels 4400. Obviously, the direction of driving rotating or return rotating is opposite between the driving units 4500a and 4500b.

It should be noted that, in other embodiments of the present invention, more driving units or more driving wheels can be arranged. In this situation, different driving units respectively push the corresponding driving wheels to rotate. As in one embodiment of the present invention, the infusion unit is provided with one driving unit and two driving wheels. The driving unit drives only one driving wheel, while the other driving wheel is used to balance the effect of force. In this case, the distance between the two driving wheels can be relatively short.

In the embodiment of the present invention, when two or more driving units are provided, by controlling the timing of different force output or by adjusting the distance between the front ends (as shown in FIG. 5) of multiple driving units, the infusion unit can improve the infusion accuracy. As shown in FIG. 10 and FIG. 11, when the driving units are both at the end of the return rotating, the distance between the front ends of the two driving portions differs by n/2 (n is an odd number) tooth pitch. At this time, when the driving wheel rotates at most ½ tooth pitch, one driving unit will reach the next driving position leading to the next rotating. Compared to a single driving unit, the infusion increment (or the infusion unit amount) is halved. In the embodiment of the present invention, n=1, 3, or 5. In order to avoid possible interference between the two adjacent driving portions, it is preferable that n=3. Only rotating at most half a pitch at one time, the driving wheel can start the next rotation. The driving unit's rotation amplitude is further reduced, and the internal structure of the infusion unit will be more compact and smaller.

Figure 12A:
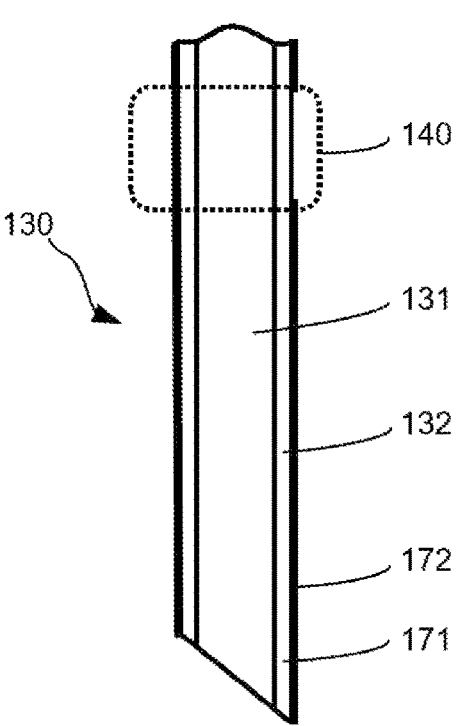
FIG. 12a-FIG. 12b are partial longitudinal cross-sectional views of an infusion cannula and an electrode according to one embodiment of the present invention.

FIG. 12a-4b are partial longitudinal cross-sectional views of the infusion cannula 130.

In an embodiment of the invention, the miniature closed-loop artificial pancreas system 100 includes a plurality of electrodes that detect analyte data. When the electrodes are conductive areas of the infusion cannula, the electrodes act as conductive-area electrodes. Or when the electrodes are disposed on the wall of the infusion cannula 130, the electrodes are cannula-wall electrodes.

In one embodiment of the invention, the cannula-wall electrode 172 is plated on the outer surface of the cannula wall of the infusion cannula 130. The cannula wall 132 of the infusion cannula 130 itself serves as a conductive-area electrode 171 also used for infusion of the drug. Generally, an insulating layer (not shown) is disposed between the conductive-area electrode 171 and the cannula-wall electrode 172 to isolate them. It will be apparent that in the embodiment of the invention, the infusion cannula 130 itself acts as both an electrode and an infusion conduit. This design reduces the number of skin punctures required to use the miniature closed-loop artificial pancreas system. With only one puncture at one place, analyte detection and drug infusion can both be completed, which reduces the risk of infection. At the same time, the method of integrally plating the electrode layer on the cannula wall 132 of the infusion cannula 130 can simplify the preparation process of the infusion cannula 130 and facilitate the process implementation.

Figure 12B:
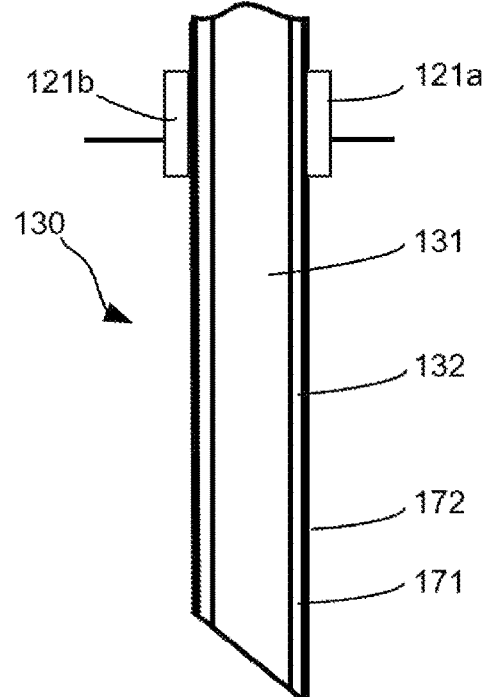

In order to facilitate electrical connection of the electrodes and electrically connective regions 121a and 121b, the electrical contact region 140 (the position of the dotted line in FIG. 12a) needs to expose the stainless steel cannula wall 132, while the other locations of the infusion cannula 130 are plated with electrode layers. As shown in FIG. 12b, when the infusion cannula 130 is mounted to the working position, the conductive-area electrode 171 and the cannula-wall electrode 172 are directly electrically connected to the electrically connective regions 121a and 121b of the input end, respectively, which allows electrical signals of the body fluid analyte data to be transmitted to program unit 120.

It should be noted that, in the embodiment of the present invention, when the infusion cannula 130 is mounted to the working position, a part of the cannula-wall electrode 172 is located in the subcutaneous tissue fluid, while another part is located above the skin, so that electrical signals can be transmitted on the cannula-wall electrode 172. The corresponding electrode arrangements in the other embodiments below have the same function and will not be described in detail later.

In the embodiment of the present invention, the miniature closed-loop artificial pancreas system 100 has only two electrodes, the conductive-area electrode 171 is a working electrode, and the cannula-wall electrode 172 is an auxiliary electrode. In another embodiment of the invention, the conductive-area electrode 171 is an auxiliary electrode while the cannula-wall electrode 172 is a working electrode. The auxiliary electrode is a counter electrode.

Figure 13A:
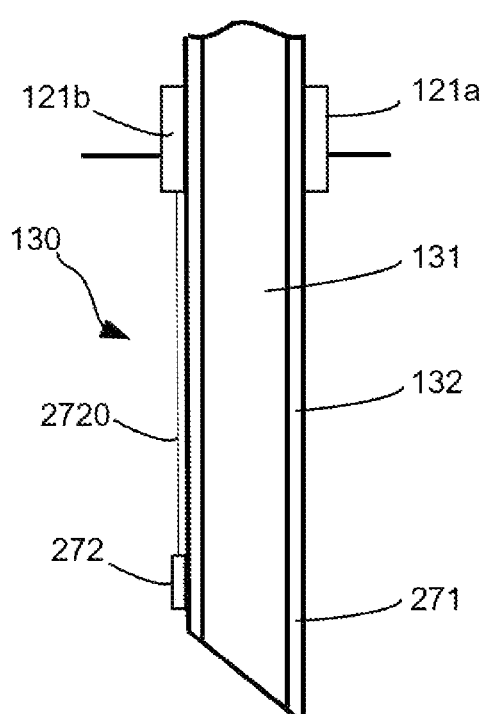
FIG. 13a-FIG. 13b are partial longitudinal cross-sectional views of an infusion cannula and an electrode in accordance with another embodiment of the present invention.

FIG. 13a-5b are partial longitudinal cross-sectional views of an infusion cannula 130 in accordance with another embodiment of the present invention. For ease of marking and narration, the electrode lead and the infusion cannula are shown separately in FIG. 13a, and the related structural illustrations below are the same as those herein, which will not be described again.

In this embodiment, the cannula wall 132 itself is a conductive-area electrode 271, the cannula-wall electrode 272 is disposed on a portion of the surface of the cannula wall 132, and the surface of the cannula wall 132 is further provided with an electrode lead 2720 electrically connected to the cannula-wall electrode 272. A layer of insulating material (not shown) is formed between the electrode lead 2720 and the cannula wall 132. When the infusion cannula 130 is mounted to the working position, the electrically connective regions 121a, 121b at the input end are electrically connected to the conductive-area electrode 271 and the electrode lead 2720, respectively. At this time, the cannula-wall electrode 272 is indirectly electrically connected to the input end, and the body fluid data signal can be transmitted to the program unit.

Figure 13B:
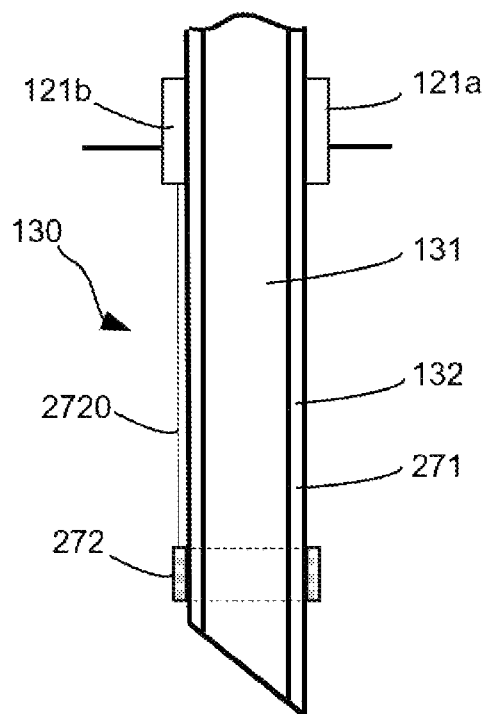

The cannula-wall electrode 272 in FIG. 13b is arranged in a ring shape, and the annular cannula-wall electrode 272 surrounds a part of the outer surface of the cannula wall 132. The cannula-wall electrode 272 may have other shapes, and is not specifically limited herein.

Figure 14:
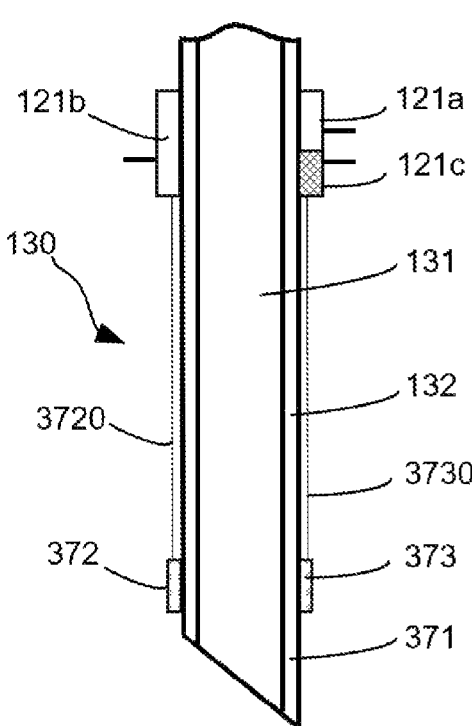
FIG. 14 is a partial longitudinal cross-sectional view of an infusion cannula and three electrodes in accordance with still another embodiment of the present invention.

FIG. 14 is a partial longitudinal cross-sectional view of an infusion cannula 130 in accordance with yet another embodiment of the present invention.

In the embodiment of the present invention, three electrodes are disposed on the infusion cannula 130: a conductive-area electrode 371, a cannula-wall electrode 372, and another cannula-wall electrode 373. The cannula wall 132 of the infusion cannula 130 itself serves as a conductive-area electrode 371, and the cannula-wall electrode 372 and 373 are respectively disposed on a portion of the outer surface of the cannula wall 132. At the same time, the surface of the cannula wall 132 is further provided with electrode leads 3720 and 3730 which are electrically connected to the cannula-wall electrodes 372 and 373, respectively. When the infusion cannula 130 is mounted to the working position, the conductive-area electrode 371, the electrode lead 3720, and the electrode lead 3730 are electrically connected to the input end's electrically connective regions 121a, 121b, and 121c, respectively, thereby realizing electrical connection between the input end and each electrode. The shape of the cannula-wall electrode 372 and 373 may be various, and is not specifically limited herein.

In the embodiment of the present invention, in order to simplify the design of the electrically connective region, the elastic member at the input end is an oriented conductive silica gel or a conductive ring. By doping different elements in the silica gel, it is possible to achieve directional conduction, such as horizontal conduction or vertical conductivity. Thus, even if 121a and 121c are adjacent to each other, the two can still be electrically insulated from each other. The electrically connective region 121b may be a conductive rubber strip or a conductive ball or the like, and is not specifically limited herein.

In the embodiment of the present invention, the conductive-area electrode 371 is a working electrode, and the cannula-wall electrode 372 and the wall electrode 373 are both auxiliary electrodes. At this time, the conductive-area electrode 371 and the cannula-wall electrode 372 or the cannula-wall electrode 373 may constitute a different electrode combination, that is, the two electrode combinations share the conductive-area electrode 371. Program unit 120 can select different electrode combinations to detect body fluid analyte data. After the electrode combination is formed, on the one hand, when a working electrode combination fails to detect, the program unit 120 can select other electrode combinations for detection according to the situation to ensure that the detection process of the body fluid signal is uninterrupted. On the other hand, the program unit 120 can select a plurality of electrode combinations to work simultaneously, perform statistical analysis on multiple sets of data of the same parameter at the same time, improve the accuracy of the analyte data, and thereby output a more accurate drug infusion signal.

Similarly, the conductive-area electrode 371 and the cannula-wall electrode 372 and 373 form one working electrode and two auxiliary electrodes, and can be arbitrarily selected according to actual needs. In another embodiment of the present invention, the conductive-area electrode 371 and the cannula-wall electrode 372 and 373 form an auxiliary electrode and two working electrodes, which can also be arbitrarily selected according to actual needs, and is not specifically limited herein.

As an embodiment of the present invention, the conductive-area electrode 371 is a working electrode, the cannula-wall electrodes 372 and 373 are auxiliary electrodes, and the cannula-wall electrodes 372 and 373 are used as a counter electrode and a reference electrode, respectively, thereby forming a three-electrode system. Similarly, the three electrodes can be arbitrarily selected according to actual needs, and are not specifically limited herein.

Also, in other embodiments of the invention, more electrodes may be provided. The system includes a plurality of working electrodes and a plurality of auxiliary electrodes, but it should be ensured that the conductive area of the infusion cannula 130 serves as at least one electrode. At this time, each electrode combination includes at least a working electrode and an auxiliary electrode, and thus a plurality of electrodes may constitute a plurality of electrode combinations. Program unit 120 may select one or more electrode combinations to detect body fluid analyte data, as desired.

Figure 15:
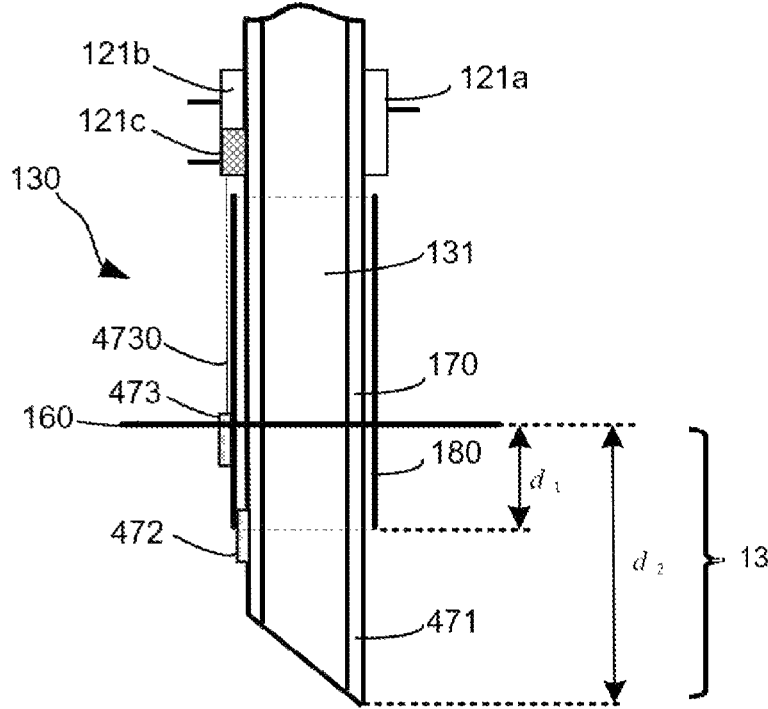
FIG. 15 is a partial longitudinal cross-sectional view showing an infusion steel needle casing hose according to still another embodiment of the present invention.

FIG. 15 is a partial longitudinal cross-sectional view of an infusion cannula 130 in accordance with yet another embodiment of the present invention. For ease of marking and description, the wall of the hose 180 of FIG. 15 is shown separated from the outer wall of the infusion steel needle 170.

In an embodiment of the invention, the infusion cannula 130 includes an infusion steel needle 170 and a hose 180 that is placed on the outer wall of the infusion steel needle 170. Setting electrodes on the surface of the hose 180 simplifies the electrode manufacture and improves the preparation efficiency. In addition, the wall material of the hose 180 can be selected according to requirements, such as the wall of the hose 180 can only allow specific analytes to pass through, weakening the interference of other substances, and improving the detection accuracy of the analyte.

The needle cavity 131 of the infusion steel needle serves as a drug infusion channel, and the wall of the infusion cannula 130 includes a steel needle wall and a hose wall. The infusion steel needle 170 itself serves as a conductive-area electrode 471, the cannula-wall electrode 472 is disposed on the outer surface of the infusion steel needle 170, and the cannula-wall electrode 473 is disposed on the outer surface of the hose 180. At this time, the cannula-wall electrode 472 is disposed in the wall of the infusion cannula 130.

In the above embodiment, the cannula-wall electrode 472 may be partially covered by the hose 180, or completely covered or the cannula-wall electrode 472 may be exposed in the tissue fluid. The cannula-wall electrode 473 may also be disposed on the inner surface of the hose 180, that is, between the steel needle wall and the hose wall, and the cannula-wall electrode 473 is electrically connected to the electrically connective region 121c through the electrode lead 4730. When the cannula-wall electrode 472 (the electrode lead of the cannula-wall electrode 472 is not shown) is partially covered or completely covered by the hose 180, or the cannula-wall electrode 473 is disposed on the inner surface of the hose 180, the wall material of the hose 180 is permeable membrane or semi-permeable membrane. Such a selection can facilitate the passage of the body fluid analyte through the wall of the hose 180, allowing the analyte to be detected by the electrode, thereby improving the flexibility of the electrode position design without affecting the detection.

In an embodiment of the invention, when the infusion cannula 130 is installed to the working position, the hose 180 and the infusion steel needle 170 have a certain relationship to the depth of penetration into the skin. Here, the depth refers to the distance from the distal end of the hose 180 or the infusion steel needle 170 which is inserted into the skin, respectively, to the surface of the skin, as shown in FIG. 15. Generally, the infusion steel needle 170 has a greater hardness than the hose 180. As shown in FIG. 15, in the range of the subcutaneous portion 13, the depth of the hose 180 into the skin is $d_1$, and the depth of the infusion steel needle 170 into the skin is $d_2$, $d_1 \leq d_2$. This design enables the infusion cannula 130 to penetrate the skin smoothly.

Figure 16A:
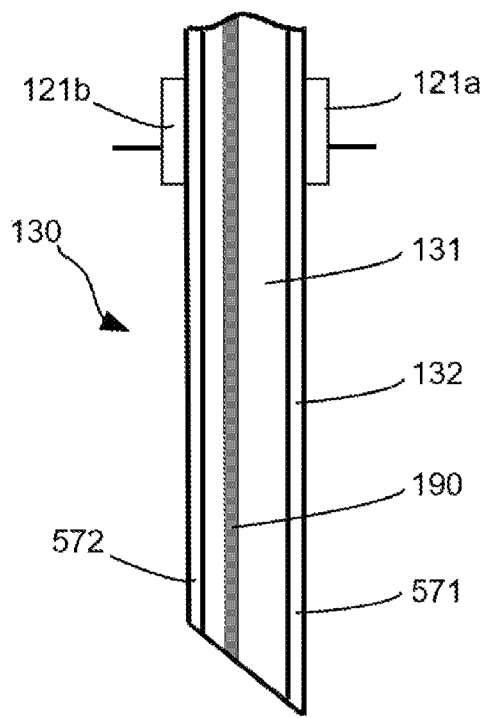
FIG. 16a is a partial longitudinal cross-sectional view of an infusion cannula having a plurality of electrically conductive areas in accordance with yet another embodiment of the present invention.

FIG. 16a-8c are partial longitudinal cross-sectional views of an infusion cannula 130 in accordance with yet another embodiment of the present invention. FIG. 16a is a longitudinal cross-sectional view of the infusion cannula 130, and FIGS. 16b and 8c are transverse cross-sectional views of the infusion cannula 130.

Figure 16B:
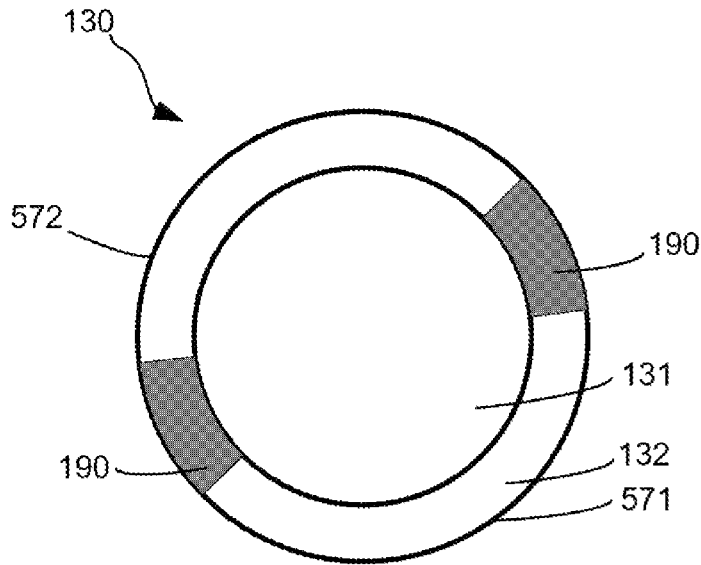
FIG. 16b-FIG. 16c are partial transverse cross-sectional views of an infusion cannula having a plurality of electrically conductive areas in accordance with yet another embodiment of the present invention.

Please refer to FIG. 16a and FIG. 16b. FIG. 16b is a schematic cross-sectional view of the infusion cannula 130 of FIG. 16a.

In an embodiment of the invention, the cannula wall 132 of the infusion cannula 130 includes a plurality of electrically conductive areas, one or more of which are used as electrodes. For example, when the cannula wall 132 includes two conductive areas, they function as the conductive-area electrode 571 and the conductive-area electrode 572, respectively. The conductive-area electrode 571 and 572 may be a working electrode and an auxiliary electrode, respectively, and are electrically connected to the electrically connective regions 121a and 121b, respectively, for electrical signal transmission. The different conductive areas of the infusion cannula itself serve as electrodes, which can further simplify the electrode design on the surface of the cannula wall and reduce the production process of the infusion cannula. The insulating portion 190 achieves electrical insulation between the two conductive areas of the infusion cannula 130.

Figure 16C:
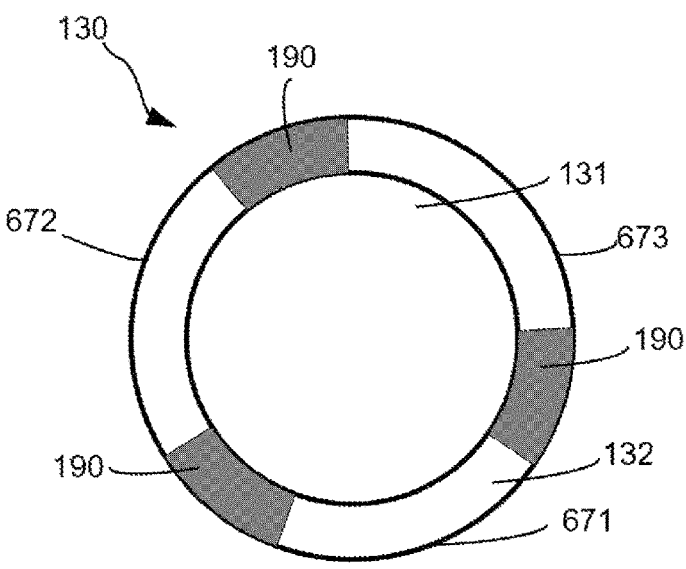

Referring to FIG. 16c, the infusion cannula 130 is integrally formed of three conductive areas, and the adjacent conductive areas are separated by the insulating portion 190. The infusion cannula 130 itself serves as three electrodes: conductive-area electrodes 671, 672 and 673, respectively. The conductive-area electrode 671 is a working electrode, and the conductive-area electrodes 672 and 673 are auxiliary electrodes, or are selected according to actual needs as described above.

Figure 17:
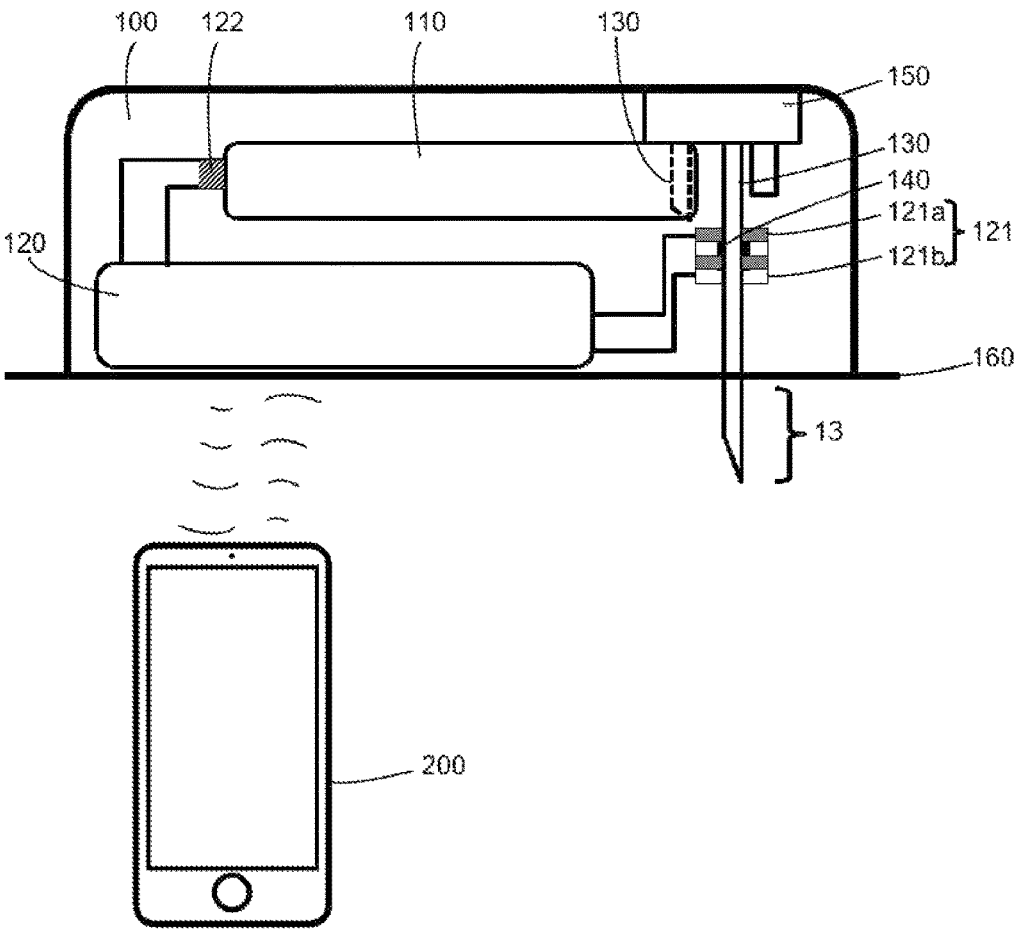
FIG. 17 is a schematic structural view of a miniature closed-loop artificial pancreas system and a remote device according to still another embodiment of the present invention.

Referring to FIG. 17, signals are transmitted between the remote device 200 and the miniature closed-loop artificial pancreas system 100.

The embodiment of the invention also includes a remote device 200. The remote device 200 includes but is not limited to a handset, a mobile terminal, or the like. The remote device 200 and the program unit 120 transmit wireless signals to each other. Program unit 120 may send body fluid analyte data or drug infusion information (including infusion or no infusion) to remote device 200. The remote device 200 can receive, record, store, display body fluid information or infusion information, as well as other functional options. The user can view historical or real-time information at any time from the remote device 200. Through the remote device 200, the user can also manually set the infusion instructions and transmit the information wirelessly to the program unit 120. Under the premise that the program unit 120 guarantees the communication security and infusion security, the infusion unit is controlled to perform the drug infusion, thereby realizing remote manual control.

In some embodiments of the invention, the miniature closed-loop artificial pancreas system 100 further includes a plurality of electrodes to form a plurality of electrode combinations as previously described. The user can manually select different electrode combinations to detect body fluid data according to the situation.

In summary, the present invention discloses a miniature closed-loop artificial pancreas system that has both infusion and detection functions to reduce the number of punctures on the skin. With only one puncture at one position, analyte detection and drug infusion can be completed, reducing the risk of infection.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A miniature closed-loop artificial pancreas system, comprising:

an infusion unit, the infusion unit includes:

a drug storage unit, a metal piece, a piston and a rigid screw, wherein the piston is arranged in the drug storage unit, and wherein the metal piece, fixedly connected to the rigid screw, is arranged on the piston;

a rotating shaft, a rotatable driving unit and a driving wheel provided with wheel teeth, wherein the rotatable driving unit includes one driving portion, and wherein the rotatable driving unit is capable of rotating around the rotating shaft, driving the driving portion to push the wheel teeth to rotate the driving wheel which drives the rigid screw forward in a non-rotating way; and a power unit and a rebound unit, wherein the power unit and the rebound unit apply forces to the rotatable driving unit respectively to make the rotatable driving unit rotate reciprocally;

at least one position detector, wherein the metal piece and the at least one position detector interact to generate electrical or magnetic signals;

a program unit, wherein the program unit comprises an input end and an output end, wherein the input end comprises a plurality of different electrically connective regions for receiving signals of analyte data in a body fluid after the output end is electrically connected to the infusion unit, wherein according to received signals of the analyte data in the body fluid, the program unit controls whether the infusion unit delivers drugs, and the program unit converts received electrical or magnetic signals into piston position information;

an infusion cannula with a conductive area, the infusion cannula is a drug infusion channel; and a plurality of electrodes for detecting the analyte data in the body fluid, wherein the plurality of electrodes comprises comprise at least one conductive-area electrode and at least one cannula-wall electrode, wherein the conductive area of the infusion cannula is one of the at least one conductive-area electrode, wherein one or more cannula-wall electrodes are located on or in a wall of the infusion cannula, wherein when the infusion cannula is installed to a working position, the infusion cannula is connected with the infusion unit, the drugs are capable of being injected into a body through the infusion cannula, and the plurality of electrodes are electrically connected to the different electrically connective regions, respectively, to input the signals of the analyte data in the body fluid to the program unit.

2. The miniature closed-loop artificial pancreas system of claim 1, wherein:

the at least one cannula-wall electrode is located on an outer surface of the wall of the infusion cannula or in the wall of the infusion cannula.

3. The miniature closed-loop artificial pancreas system of claim 2, wherein:

the at least one cannula-wall electrode is located on the outer surface of the wall of the infusion cannula, and when the infusion cannula is installed to the working position, the at least one conductive-area electrode and the at least one cannula-wall electrode are directly electrically connected to the different electrically connective regions, respectively.

4. The miniature closed-loop artificial pancreas system of claim 3, wherein the at least one cannula-wall electrode is located on a subcutaneous part of the outer surface of the wall of the infusion cannula, and the outer surface of the wall of the infusion cannula is further provided with an electrode lead electrically connected to the at least one cannula-wall electrode, such that when the infusion cannula is installed to the working position, the electrode lead and the at least one conductive-area electrode are electrically connected to the different electrically connective regions, respectively.

5. The miniature closed-loop artificial pancreas system of claim 2, wherein:

the infusion cannula includes an infusion steel needle and a hose which is placed on an outer wall surface of the infusion steel needle, and a needle cavity of the infusion steel needle is used for infusion of the drugs.

6. The miniature closed-loop artificial pancreas system of claim 5, wherein:

when the infusion cannula is installed to the working position, a depth of the hose into a skin is $d_1$, a depth of the infusion steel needle into the skin is $d_2$, and $d_1 \leq d_2$.

7. The miniature closed-loop artificial pancreas system of claim 6, wherein:

the infusion steel needle is the at least one conductive-area electrode, and the at least one cannula-wall electrode is located on an outer or inner surface of the hose wall or is located on the outer wall surface of the infusion steel needle.

8. The miniature closed-loop artificial pancreas system of claim 7, wherein:

when the infusion cannula is installed to the working position, the at least one cannula-wall electrode that is located on the outer wall surface of the infusion steel needle is exposed in a subcutaneous tissue fluid or covered in whole or in part by the hose.

9. The miniature closed-loop artificial pancreas system of claim 7, wherein:

when the at least one cannula-wall electrode that is located on the outer wall surface of the infusion steel needle is covered in whole or in part by the hose, or when the at least one cannula-wall electrode is located on the inner surface of the hose wall, the hose wall is a permeable membrane or a semi-permeable membrane.

10. The miniature closed-loop artificial pancreas system of claim 7, wherein the plurality of electrodes include at least one working electrode and at least one auxiliary electrode.

11. The miniature closed-loop artificial pancreas system of claim 10, wherein the at least one conductive-area electrode is the at least one working electrode or the at least one auxiliary electrode.

12. The miniature closed-loop artificial pancreas system of claim 11, wherein the plurality of electrodes form one or more electrode combinations, each electrode combination comprising the at least one working electrode and the at least one auxiliary electrode, the program unit choosing the one or more electrode combinations to detect the analyte data in the body fluid.

13. The miniature closed-loop artificial pancreas system of claim 12, further comprising:

a remote device, the remote device and the program unit being configured to transmit wireless signals to each other, the program unit being configured to transmit the analyte data or drug infusion information to the remote device, and the remote device configured to send a manually selected electrode combination for detection or the drug infusion information to the program unit.

14. The miniature closed-loop artificial pancreas system of claim 10, wherein the at least one auxiliary electrode is at least one counter electrode, or the at least one auxiliary electrode includes the at least one counter electrode and a reference electrode.

15. The miniature closed-loop artificial pancreas system of claim 2, wherein the infusion cannula comprises a plurality of electrically conductive areas isolated from each other, the plurality of electrically conductive areas comprising a plurality of electrically conductive-area electrodes.

16. The miniature closed-loop artificial pancreas system of claim 1, wherein the input end is an elastic member, and the elastic member comprises one of or a combination of a conductive strip, an oriented conductive silica gel, a conductive ring, and a conductive ball.

17. The miniature closed-loop artificial pancreas system of claim 1, wherein:

the infusion unit includes a plurality of infusion subunits, the plurality of infusion subunits being electrically connected to the output ends, respectively, and the program unit controlling whether each infusion subunit delivers the drugs.

18. The miniature closed-loop artificial pancreas system of claim 1, wherein:

the miniature closed-loop artificial pancreas system is composed of a plurality of parts, the infusion unit and the program unit are arranged in different parts, and the different parts are connected by a waterproof plug.

19. The miniature closed-loop artificial pancreas system of claim 1, wherein the rigid screw is a metal screw, and the metal piece is electrically connected with the metal screw, so that the metal piece and a corresponding one of the at least one position detector together constitute a capacitor, and a linear movement of the metal piece causes a change in capacitance making the corresponding position detector generate an electrical signal.

20. The miniature closed-loop artificial pancreas system of claim 1, wherein:

the metal piece is a magnetic metal piece, and the at least one position detector is a magnetic induction detector, wherein a linear movement of the magnetic metal piece causes a change in a magnetic field around each position detector making each position detector generate a magnetic signal.

21. The miniature closed-loop artificial pancreas system of claim 1, wherein a direction in which the power unit applies the forces to the rotatable driving unit is parallel to a forward direction of the rigid screw.

22. The miniature closed-loop artificial pancreas system of claim 1, wherein:

the infusion unit includes a total of two rotatable driving units; and the two rotatable driving units are coaxial or are respectively disposed on two sides of the driving wheel.

23. The miniature closed-loop artificial pancreas system of claim 1, wherein:

the infusion unit further includes a clutch structure movably disposed on the driving wheel, the rigid screw passes through the clutch structure, the clutch structure is provided with an internal thread that cooperates with the rigid screw, and the driving wheel drives the clutch structure to rotate which, with the internal thread, drives the rigid screw forward in a non-rotating way.

24. The miniature closed-loop artificial pancreas system of claim 1, wherein:

the infusion unit further includes a blocking wall, and the rotatable driving unit stops rotating upon contacting the blocking wall.

* * * * *